US012303675B1

(12) United States Patent
Denyer et al.

(10) Patent No.: US 12,303,675 B1
(45) Date of Patent: May 20, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,625

(22) Filed: Aug. 29, 2024

(51) Int. Cl.
*A61M 5/32* (2006.01)
*A61M 5/20* (2006.01)

(52) U.S. Cl.
CPC .......... *A61M 5/326* (2013.01); *A61M 5/3243* (2013.01); *A61M 2005/2013* (2013.01); *A61M 2005/208* (2013.01); *A61M 2005/3247* (2013.01); *A61M 2005/3268* (2013.01)

(58) Field of Classification Search
CPC ................ A61M 5/3243; A61M 5/326; A61M 2005/2013; A61M 2005/206; A61M 2005/208; A61M 2005/3247; A61M 2005/3261; A61M 2005/3263; A61M 2005/3267; A61M 2005/3268
See application file for complete search history.

(56) References Cited

U.S. PATENT DOCUMENTS

| 4,118,611 | A | 10/1978 | Harris |
| 5,609,577 | A | 3/1997 | Haber et al. |
| 5,743,888 | A | 4/1998 | Wilkes et al. |
| 6,261,264 | B1 | 7/2001 | Tamaro |
| 10,765,811 | B2 | 9/2020 | Vedrine et al. |
| 10,926,040 | B2 | 2/2021 | Karasawa |
| 2004/0044318 | A1 | 3/2004 | Fiser et al. |
| 2005/0171477 | A1 | 8/2005 | Rubin et al. |

(Continued)

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

*Primary Examiner* — Kami A Bosworth
(74) *Attorney, Agent, or Firm* — Fish & Richardson P.C.

(57) ABSTRACT

A medicament delivery device comprises a housing, a needle, a needle cover, a needle cover biasing member, a skin sensor, a skin sensor biasing member, and a retaining mechanism. The needle cover is axially movable between an extended position and a retracted position. The needle cover biasing member is configured to bias the needle cover towards the extended position. The skin sensor extends from the distal end of the needle cover and is configured to contact an injection site. The skin sensor biasing member is configured to bias the skin sensor from a proximal position to a distal position away from the needle cover. The retaining mechanism is configured to temporarily retain the needle cover in the retracted position and transfer at least a part of the force of the needle cover biasing member to the housing to prevent the needle cover biasing member from moving the needle cover distally.

14 Claims, 5 Drawing Sheets

(56) References Cited

U.S. PATENT DOCUMENTS

| | | |
|---|---|---|
| 2011/0276029 A1 | 11/2011 | Field |
| 2012/0101475 A1 | 4/2012 | Wilmot et al. |
| 2016/0271319 A1* | 9/2016 | Bengtsson .......... A61M 5/3204 |
| 2018/0200487 A1 | 7/2018 | Sokolski et al. |
| 2022/0288318 A1* | 9/2022 | Plambech .......... A61M 5/2033 |
| 2024/0198013 A1* | 6/2024 | Laurence .......... A61M 5/3245 |

OTHER PUBLICATIONS

Speciale et al., "Snap-Through Buckling Mechanism for Frequency-up Conversion in Piezoelectric Energy Harvesting," Applied Sciences, May 23, 2020, 10(10):3614, 18 pages.
U.S. Appl. No. 18/818,944, filed Aug. 29, 2024, Timothy Denyer.
U.S. Appl. No. 18/819,383, filed Aug. 29, 2024, Timothy Denyer.
U.S. Appl. No. 18/819,704, filed Aug. 29, 2024, Timothy Denyer.

\* cited by examiner

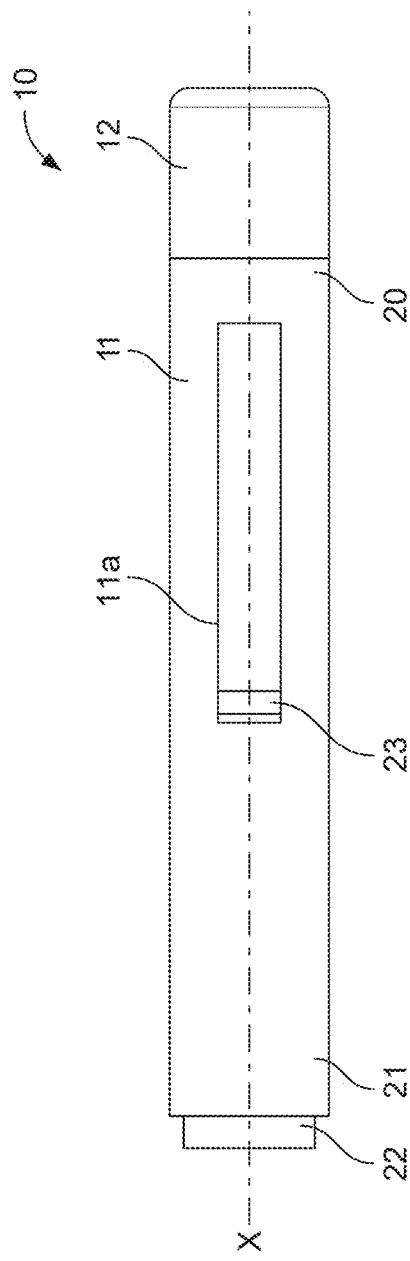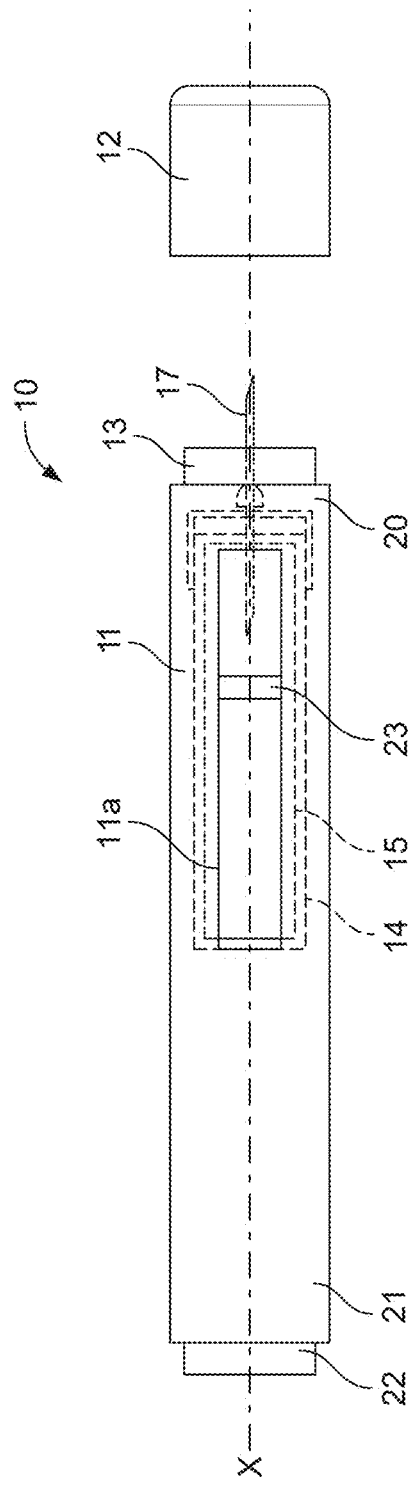
FIG. 1A
FIG. 1B

MEDICAMENT DELIVERY DEVICE

TECHNICAL FIELD

This application relates to a medicament delivery device.

BACKGROUND

Medicament delivery devices are used to deliver a range of medicaments.

In some devices, the device must be held in a holding position at an injection site for a predetermined period of time, to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

The present disclosure provides an improved medicament delivery device.

SUMMARY

According to a first aspect of the present disclosure, there is provided a medicament delivery device comprising a housing comprising a proximal end and a distal end, a needle and a needle cover, wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover, a needle cover biasing member configured to bias the needle cover axially in the distal direction towards the extended position, a skin sensor extending distally from the distal end of the needle cover and configured to contact an injection site, a skin sensor biasing member acting between the needle cover and the skin sensor, the skin sensor biasing member being configured to bias the skin sensor axially in the distal direction from a proximal position to a distal position away from the needle cover, a retaining mechanism configured to temporarily retain the needle cover in the retracted position and temporarily transfer at least a part of the force of the needle cover biasing member to the housing such that the needle cover biasing member is prevented from moving the needle cover distally.

One advantage of this arrangement is that once the needle cover has been moved to the retracted position, the holding force required to overcome the distally acting force of the needle cover biasing member is reduced, if not completely eliminated. This may be particularly advantageous for users that lack strength to hold a medicament delivery device against the force of a needle cover biasing member for longer periods of time.

In some embodiments, the retaining mechanism may be configured to transfer substantially the full force of the needle cover biasing member to the housing when the needle cover is in the retracted position and the skin sensor is in the proximal position.

Thus, the holding force required to overcome the distally acting force of the needle cover biasing member may be completely eliminated.

In some embodiments, the retaining mechanism may comprise a proximally extending arm of the needle cover, the arm may comprise a projection on its proximal end, and a catch may be located on the inner surface of the housing, wherein the projection may be configured to engage the catch when the needle cover is in its retracted position.

Thus, the biasing force of the needle cover biasing member can be transferred to the housing to reduce the holding force required by the operator.

In some embodiments, the proximal end of the arm of the needle cover may be deflectable in a radially inward direction.

Thus, the projection of the arm may be deflected so that it can be moved past the catch when the needle cover is moved in the proximal direction towards its retracted position.

In some embodiments, the projection may comprise an inclined engaging surface. In some embodiments, the proximal end of the arm of the needle cover may be biased radially inwards.

Thus, the projection is able to slide against the catch to allow the projection to move radially inwardly to disengage from the catch when the reinforcing member has been moved distally relative to the needle cover such that the reinforcing member is no longer reinforcing the arm of the needle cover.

In some embodiments, the retaining mechanism may further comprise a proximally extending reinforcing member of the skin sensor configured to prevent the projection disengaging from the catch when the needle cover is held in the retracted position and the skin sensor is held in the proximal position.

Thus, the reinforcing member can hold the needle cover in place against the housing and cause the biasing force of the needle cover biasing member to be transferred to the housing to reduce the holding force required by the operator.

In some embodiments, the reinforcing member of the skin sensor may be located radially inwards of the arm of the needle cover.

Therefore, the reinforcing member can prevent radial inwards movement of the arm of the needle cover, and thus prevent the arm of the needle cover from disengaging the catch of the housing.

In some embodiments, the needle cover may comprises an annular member having a slot adjacent to the arm, wherein the reinforcing member of the skin sensor may extend and is moveable axially through the slot.

Thus, the skin sensor may be located both radially inward and distally of the needle cover whilst also still being able to position the reinforcing member radially inwardly of the arm of the needle cover to retain the projection against the catch when the needle cover is in the retracted position.

In some embodiments, the reinforcing member of the skin sensor may be stiffer than the arm of the needle cover.

Thus, the reinforcing member may be able to provide the force required to withstand the biasing force of the needle cover biasing member. That is, the reinforcing member may prevent inward movement of the arm of the needle cover. In addition, this means that the stiffness of the arm of the needle cover can be reduced so that it is easier for the needle cover to disengage the housing once the reinforcing member has been moved distally relative to the needle cover.

In some embodiments, upon depression of the device against an injection site, the skin sensor may be configured to be moved from the distal position to the proximal position before the needle cover is moved from the extended position to the retracted position.

In some embodiments, the spring rate of the needle cover biasing member may be greater than the spring rate of the skin sensor biasing member.

In some embodiments, the spring rate of the needle cover biasing member may be the same as the spring rate of the skin sensor biasing member, and the needle cover biasing member may have a greater amount of initial compression than the skin sensor biasing member when needle cover is in the extended position and the skin sensor is in the distal position relative to the needle cover.

Therefore, the skin sensor may be moved into its proximal position relative to the needle cover before the needle cover is moved from its extended position. This allows the retaining mechanism to be primed before the needle is inserted into the injection site.

In some embodiments, the needle cover biasing member and/or the skin sensor biasing member may be coil springs.

In some embodiments, the medicament delivery device may be configured to inject greater than 2 ml of medicament and/or wherein the medicament delivery device is configured to inject medicament having a viscosity of greater than 25 cP.

In some embodiments, the medicament delivery device may further comprise a needle cover lock configured to prevent proximal movement of the needle cover once the needle cover is in the extended position post-use.

Therefore, after use, the needle cover may permanently cover the needle to prevent an accidental contact with the used needle.

In some embodiments, the medicament delivery device may comprise medicament.

The medicament delivery device may comprise a container for containing the medicament. The medicament may be located in the container. The container may be a syringe. The syringe may comprise the needle. The container may be a cartridge which is initially separated from the needle when the needle cover is in the extended position.

In a second aspect of the present disclosure, there is provided a method of preparing a medicament delivery device for use, the method comprising moving a skin sensor proximally from a distal position to a proximal position against the force of a skin sensor biasing member, moving the skin sensor and a needle cover proximally from an extended position to a retracted position within a housing, engaging a projection on an arm of the needle cover with a catch located in the housing and maintaining the projection in engagement with the catch with a reinforcing member of the skin sensor, wherein engaging the needle cover with the housing transfers the force of the needle cover biasing member to the housing.

In a third aspect of the present disclosure, there is provided a method of extending a needle cover of a medicament delivery device after medicament has been dispensed from the medicament delivery device, the method comprising removing the medicament delivery device from an injection site, moving the skin sensor distally from a proximal position to a distal position under the force of a skin sensor biasing member, disengaging a projection of a needle cover from a catch located in a housing, moving the needle cover in the distal direction from a retracted position to an extended position;

In some embodiments, the method further comprises the step of engaging a locking mechanism to prevent proximal movement of the needle cover.

BRIEF DESCRIPTION OF THE DRAWINGS

Embodiments will now be described, by way of example only, with reference to the accompanying drawings, in which:

FIG. 1A shows an injector device with a cap attached;

FIG. 1B shows the injector device of FIG. 1A with the cap removed;

DETAILED DESCRIPTION

Figure 2:
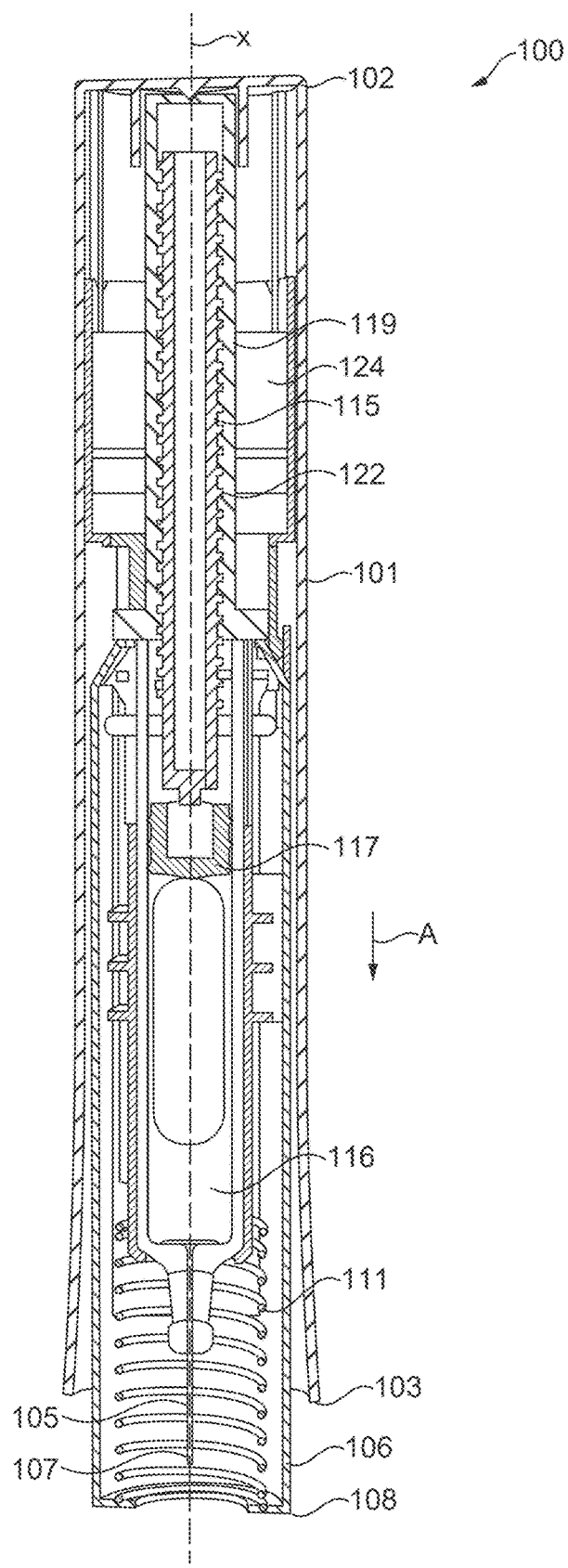
FIG. 2 shows a simplified schematic cross-sectional side view of a medicament delivery device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component.

Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23.

Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11. Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 shows a simplified view of a medicament delivery device 100. The medicament delivery device 100 comprises a housing 101. The housing 101 comprises a proximal end 102 and a distal end 103. The medicament delivery device 101 further comprises a needle 105 for injecting medicament and a needle cover 106. The needle 105 has a distal end 107. The needle cover 106 is axially movable relative to the housing 101 between an extended position, in which the needle cover 106 extends from the distal end 103 of the housing 101 and covers the distal end 107 of the needle 105, and a retracted position, in which the needle cover 106 is located in a proximal position relative to the extend position such that the needle 105 protrudes from a distal end 108 of the needle cover 106 . . . . The medicament delivery device 100 extends along an axis X.

The medicament delivery device 100 is shown in the extended position in FIG. 2. The extended position may be the initial position in which the medicament delivery device 100 is provided.

The medicament delivery device 100 further comprises a needle cover biasing member 111. The needle cover biasing member 111 is configured to bias the needle cover 106 axially in the distal direction towards the extended position. The distal direction is indicated by the direction of the arrow A in FIG. 2. In some embodiments, the needle cover biasing member 111 may be a spring.

The medicament delivery device 100 may further comprise a plunger rod 115. The plunger rod 115 may be axially moveable within the housing 101. The medicament delivery device 100 may further comprise a syringe 116. The syringe 116 may be configured to contain medicament. The syringe 116 may comprise the needle 105 located on a distal end of the syringe 116. The plunger rod 115 may be axially movable within a syringe 116 of the medicament delivery device 100 to dispense medicament from the syringe 116 via the needle 105. The syringe 116 may comprise a piston 117.

The plunger rod 115 may act on the piston to dispense medicament from the syringe 116 via the needle 105.

The medicament delivery device 100 may further comprise a collar 119. The collar 119 may be axially fixed relative to the housing 101. The collar 119 may interfaces with the plunger rod 115 via a screw thread 122. The medicament delivery device 100 may further comprise a drive member 124. The drive member 124 may be a biasing member that is configured to rotate the collar 119 when the drive member 124 is released. The drive member 124 may be a rotational biasing member, such as a spring. The spring 124 may be a torsion spring. The torsion spring 124 may be released when the needle cover 106 reaches a predetermined axial displacement in the proximal direction with a release mechanism (not shown). The rotation of the collar 119 may cause the plunger rod 115 to move distally within the syringe 116, in view of the screw thread 122, to thereby dispense medicament from the syringe 116 via the needle 105.

The needle cover 106 may be moved axially into the housing 101 uncovering the needle 105. The needle cover 106 may be moved proximally by being pressed against an injection site 125. The proximal axial displacement of the needle cover 106 may cause the release of the spring 124 which rotates the collar 119. The rotation of the collar 119 may move the plunger rod 115 axially in the distal direction within the syringe 116 to dispense the medicament via the needle 105.

The medicament delivery device 100 may be pressed against the injection site 125, to hold the needle cover 106 in the retracted position whilst the medicament is dispensed from the medicament delivery device 100. In known medicament delivery devices, the user must hold the medicament delivery device 100 against the injection site 125 against the force of the needle cover biasing member 111.

After the medicament has been dispensed, the medicament delivery device 100 is removed from the injection site 125. The needle cover 106 may move distally under the force of the needle cover biasing member 111 to a locked position. In the locked position, the needle cover 106 covers the distal end 107 of the needle 105. In the locked position, the needle cover 106 may be prevented from moving proximally.

The medicament delivery device 100 may be configured to inject greater than 2 ml of medicament and/or the medicament delivery device 100 is configured to inject medicament having a viscosity of greater than 25 cP.

Figure 3:
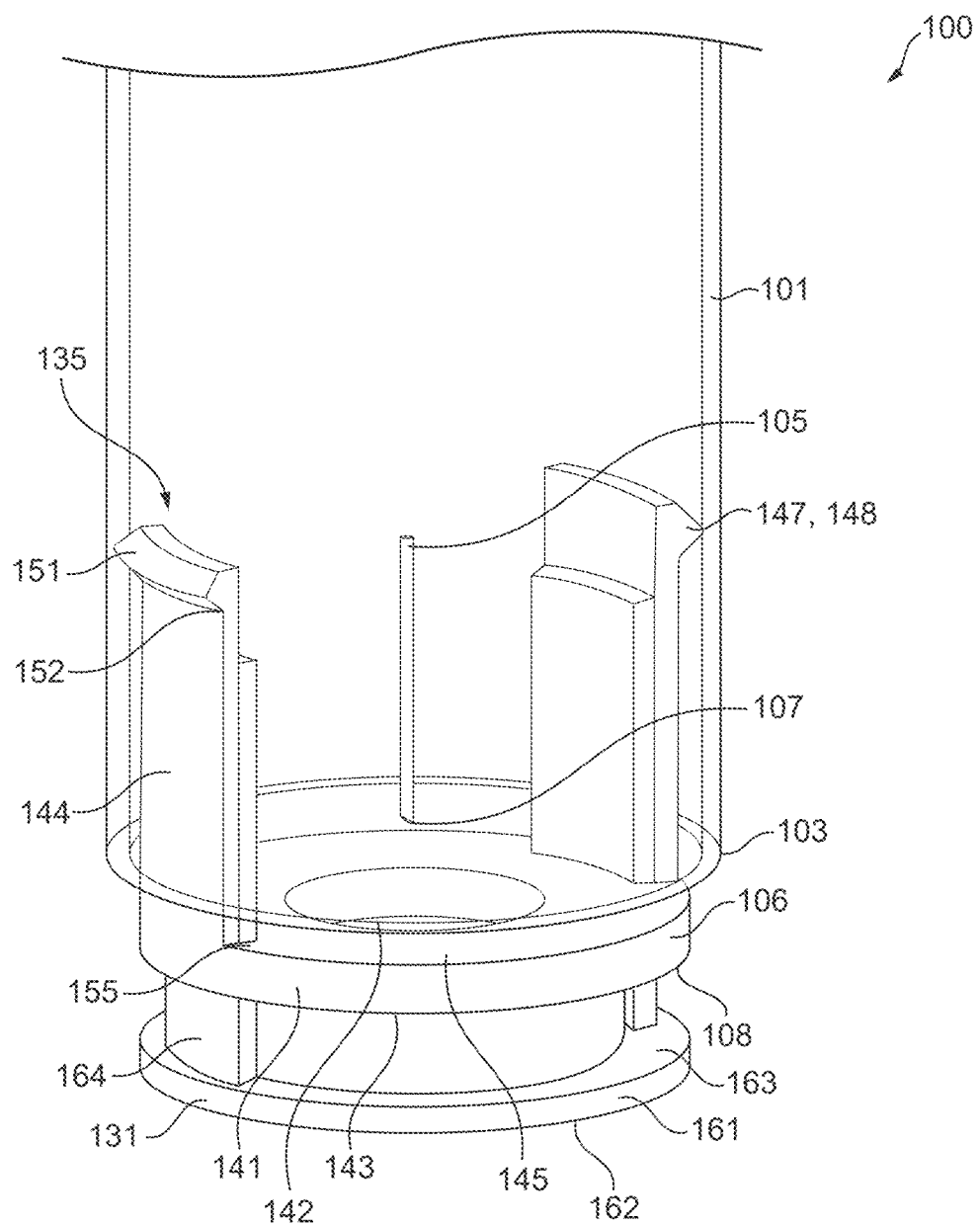
FIG. 3 shows a schematic perspective view of components of a medicament delivery device.

FIG. 3 shows a simplified schematic perspective view of components of the medicament delivery device 100 and FIGS. 4A to 4E show simplified schematic side cross-sectional views of a medicament delivery device 100 at various stages of operation of the medicament delivery device 100. To reduce complexity and replication of subject-matter in the drawings, the cross-sections shown in FIGS. 4A to 4E show only on lateral half of the distal end of the medicament delivery device 100. The features described and/or contemplated in relation to the medicament delivery device 100 may be incorporated in the medicament delivery device 100 described and/or contemplated above. In the following described embodiment, the feature relating to the needle cover 106 and needle cover biasing member 111 are modified compared to the medicament delivery device 100 shown in FIG. 2.

The medicament delivery device 100 comprises a housing 101. The housing 101 comprises a proximal end (not shown in FIGS. 3 and 4A to 4E) and a distal end 103. The medicament delivery device 100 further comprises a needle 105 and a needle cover 106. The needle cover 106 is axially moveable between an extended position, shown in FIG. 4A, and a retracted position, shown in FIG. 4C.

Figures 4A, 4B:
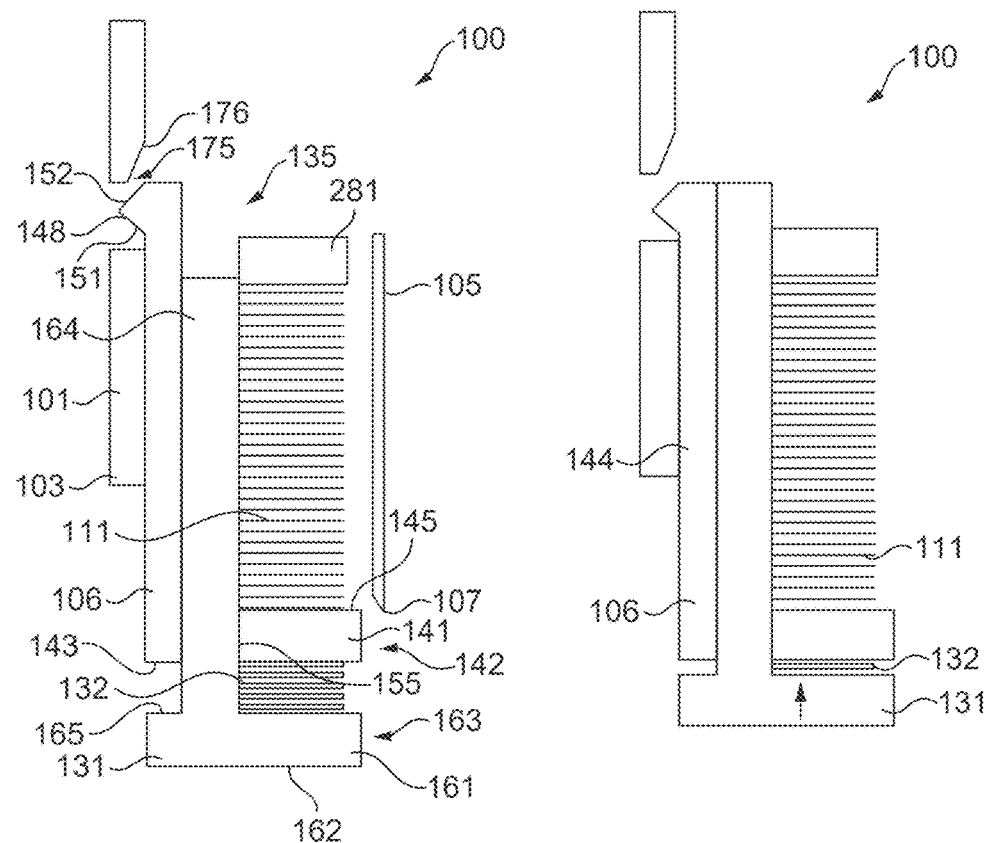
FIGS. 4A to 4E show schematic side views of components of a medicament delivery device at various stages of operation.

In the extended position, the needle cover 106 extends from the distal end 103 of the housing 101 and covers a distal end 107 of the needle 105, as shown in FIG. 4A. In the retracted position, the needle cover 106 is located in a proximal position relative to the extended position. In the retracted position, the needle cover is proximally located such that the needle 105 protrudes from a distal end 108 of the needle cover 106. The medicament delivery device 100 also comprises a needle cover biasing member 111. The needle cover biasing member 111 is configured to bias the needle cover 106 axially in the distal direction towards the extended position.

The medicament delivery device 100 comprises a skin sensor 131. The skin sensor 131 extends distally from the distal end of the needle cover 106. The skin sensor 131 is configured to contact an injection site 125. Furthermore, the medicament delivery device 100 also comprises a skin sensor biasing member 132. The skin sensor biasing member 132 is configured to bias the skin sensor 131 axially in the distal direction towards a distal position away from the needle cover 206.

The medicament delivery device 100 further comprises a retaining mechanism 135. The retaining mechanism 135 is configured to temporarily retain the needle cover 106 in the retracted position and temporarily transfer at least a part of the force of the needle cover biasing member 111 to the housing 101. Thus, the needle cover biasing member 111 is prevented from moving the needle cover 111 distally.

One advantage of this arrangement is that once the needle cover 106 has been moved to the retracted position, the holding force required to overcome the distally acting force of the needle cover biasing member 111 is reduced, if not completely eliminated. This may be particularly advantageous for users that lack strength to hold a medicament delivery device against the force of a needle cover biasing member for longer periods of time.

Figure 4C:
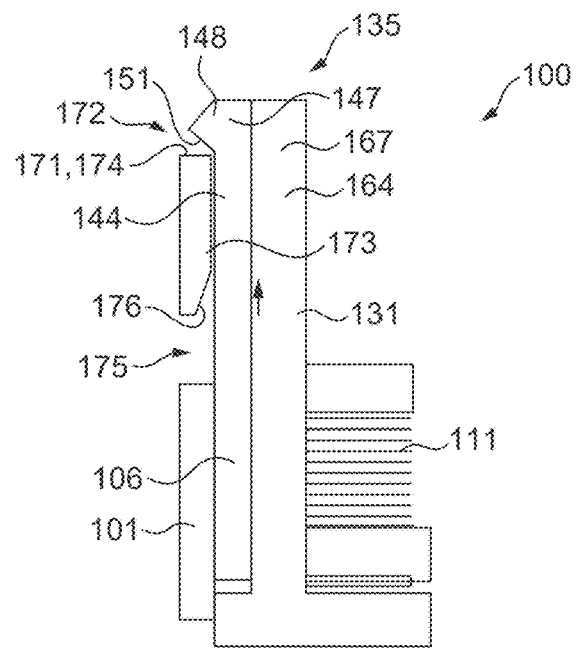

In some embodiments, the retaining mechanism 135 may be configured to transfer substantially the full force of the needle cover biasing member 111 to the housing 101 when the needle cover 106 is in the retracted position and the skin sensor is in the proximal position, as shown in FIG. 4C.

In some embodiments, the spring rate of the needle cover biasing member 111 may be greater than the spring rate of the skin sensor biasing member 132. Therefore, the skin sensor biasing member 132 may be compressed before the needle cover biasing member 111 is compressed. When the needle cover 106 is in its retracted position and the skin sensor 131 is in its proximal position relative to the needle cover 106, the distal end of the needle 105 may extend beyond the distal end of the skin sensor 131.

In some embodiments, the spring rate of the needle cover biasing member 111 may be the same as the spring rate of the skin sensor biasing member 132. In such embodiments, the initial compressions of the needle cover biasing member 111 and the skin sensor biasing member 132 may be different. For example, the needle cover biasing member 111 may have a greater amount of initial compression than the skin sensor biasing member 132. Therefore, upon an operator pushing the medicament delivery device 100 against an injection site, only the skin sensor biasing member 132 may be compressed initially, leading to proximal movement of the skin sensor 131 relative to the needle cover 106.

Referring to FIG. 3 and FIG. 4A, the needle cover 106 may comprise a body portion 141. The body portion 141 of the needle cover 106 may be the distal-most portion of the needle cover 106. The body portion 141 of the needle cover 106 may extend circumferentially about the central longitudinal axis X of the medicament delivery device 100, as shown in FIG. 3. The body portion 141 of the needle cover 106 may be configured to prevent access to the needle 105 when the needle cover 106 is in the extended position. This may help to prevent accidental contact with the needle 105.

The body portion 141 of the needle cover 106 may be annular. That is, the body portion 141 of the needle cover 106 may comprise an aperture 142. The aperture 142 may be located centrally in the body portion 141 of the needle cover 106. The aperture 142 may extend through the full thickness of the body portion 141 in a direction parallel to the longitudinal axis X of the medicament delivery device 100. The aperture 142 may be configured to allow the needle 105 to extend therethrough when the needle cover 106 is in the retracted position. The body portion 141 may also be referred to as an annular member.

The needle cover 106 may further comprise an arm 144. The arm 144 of the needle cover 106 may extend in the proximal direction. The arm 144 may extend proximally from the body portion 141 of the needle cover 106. That is, the arm 144 of the needle cover 106 may extend proximally from a proximal facing surface 145 of the body portion 141 of the needle cover 106. The arm 144 may extend from the periphery of the body portion 141 of the needle cover 106.

The arm 144 may be elongate such that the length dimension of the arm is greater than the width and thickness dimensions of the arm 144. The arm 144 may extend around only a section of the circumference of the body portion 141 of the needle cover 106, for example, but not limited to 10 to 20% of the circumference of the needle cover 106. Therefore, the arm 144 may extend arcuately around the longitudinal axis X of the medicament delivery device 100.

The arm 144 may comprise a proximal end 147 spaced from the body portion 141 of the needle cover 106. The proximal end 147 of the arm 144 may comprise a projection 148. The projection 148 may form a latch 148, as will be explained in more detailed hereinafter. The projection 148 may extend radially outwards from the proximal end 147 of the arm 144 of the needle cover 106.

In some embodiments, the projection 148 may have a first engaging surface 151 and a distal engaging surface 152. The first engaging surface 151 of the projection 148 may be generally distally facing. In some embodiments, the first engaging surface 151 may be inclined relative to the plane extending perpendicular to the longitudinal axis X of the medicament delivery device 100 when the needle cover 106 is in the extended position, as shown in FIG. 4A. However, it will be appreciated that in some embodiments, the first engaging surface 151 may extend perpendicularly to the longitudinal axis X of the medicament delivery device 100. The second engaging surface 152 of the projection 148 may be generally proximally facing. The second engaging surface of the projection 148 may be inclined relative to the plane extending perpendicular to the longitudinal axis X of the medicament delivery device 100. In some embodiments, the projection 148 may be generally triangular in cross-section.

In some embodiments, as shown in FIG. 4A, the arm 144 of the needle cover 106 may extend proximally parallel to the longitudinal axis of medicament delivery device 100 when the needle cover is in the extended position. The arm 144 of the needle cover 106 may be deflectable in a radially inward direction, i.e. toward the central longitudinal axis X of the medicament delivery device 100. The arm 144 of the needle cover 106 may be resiliently deflectable such that it returns to its original parallel alignment with the longitudinal axis X once the external deflecting force is removed.

However, it will be appreciated that in an alternative embodiment, a portion of the arm 144 proximate the proximal end 147 of the arm 144 may be biased radially inwards.

In some embodiments, the needle cover 106 may further comprise a slot 155. The slot 155 may extend through the thickness of the body portion 141 of the needle cover 106 in the longitudinal direction X of the medicament delivery device 100.

The slot 155 may be configured to receive a portion of the skin sensor 131, as will be explained in more detail hereinafter. In some embodiments, the slot 155 may be arcuate. That is, the slot 155 may extend in the circumferential direction. The slot 155 may be located radially inward of the arm 144 of the needle cover 106. In some embodiments, the slot 155 in the body portion 141 of the needle cover 106 may be located radially adjacent to the point at which the arm 144 extends proximally from the body portion 141 of the needle cover 106.

As shown in FIG. 3, the needle cover 106 may comprise a plurality of arms 144.

The plurality of arms 144 may be spaced circumferentially about the body portion 141 of the needle cover 106. The plurality of arms 144 may be spaced equidistantly about the longitudinal axis X of the medicament delivery device 100. In embodiments where two arms 144 are present, the arms may be located diametrically opposite each other. In addition, the needle cover 106 may comprise a plurality of slots 155. The number of slots 155 may be equal to the number of arms 144.

Referring to FIG. 3 and FIG. 4A, the skin sensor 131 may comprise a body portion 161. The body portion 161 of the skin sensor 131 may be the distal-most portion of the skin sensor 131. The skin sensor 131 may comprise a distal facing surface 162. The distal facing surface 162 may be configured to be place against an injection site. The body portion 131 of the skin sensor 131 may extend circumferentially about the central longitudinal axis X of the medicament delivery device 100, as shown in FIG. 3.

The body portion 161 of the skin sensor 131 may be annular. That is, the body portion 161 of the skin sensor 131 may comprise an aperture 163. The aperture 163 may be located centrally in the body portion 141 of the skin sensor 131. The aperture 163 may extend through the full thickness of the body portion 161 in a direction parallel to the longitudinal axis X of the medicament delivery device 100. The aperture 163 may be configured to allow the needle 105 to extend therethrough when the skin sensor 131 is in the proximal position and the needle cover 106 is in the retracted position.

The skin sensor 131 may further comprise a reinforcing member 164. The reinforcing member 164 of the skin sensor 131 may extend in the proximal direction. The reinforcing member 164 may extend proximally from the body portion 161 of the skin sensor 131. That is, the reinforcing member 164 of the skin sensor 131 may extend proximally from a proximal facing surface 165 of the body portion 161 of the skin sensor 131.

The reinforcing member 164 may be elongate such that the length dimension of the reinforcing member 164 is greater than the width and thickness dimensions of the reinforcing member 164. The reinforcing member 164 may extend around only a section of the circumference of the body portion 161 of the skin sensor 131, for example, but not limited to 10 to 20% of the circumference of the skin sensor 131. Therefore, the reinforcing member 164 may extend arcuately around the longitudinal axis X of the medicament delivery device 100.

The reinforcing member 164 may comprise a proximal end 167 spaced from the body portion 161 of the skin sensor 131. The proximal end 167 of the reinforcing member 164 may be configured to be located at the same axial point within the medicament delivery device 100 as the proximal end 147 of the arm 144 of the needle cover 106 when the skin sensor 131 is in its proximal position, as shown in FIG. 4B and FIG. 4C, as will be explained in more detail hereinafter, Therefore, in some embodiments, the length dimension of the reinforcing member 164 of the skin sensor 131 may be greater than the length dimension of the arm 144 of the needle cover 106. In some embodiments, the reinforcing member 164 may have similar width dimensions to the arm 144 of the needle cover 106. In some embodiments, the reinforcing member 164 may have similar or greater thickness dimensions (in the radial direction) to the arm 144 of the needle cover 106.

In some embodiments, the reinforcing member 164 of the skin sensor 131 may have a length that is greater than the length of the arm 144 of the needle cover 106 such that the proximal end 167 of the reinforcing member 164 is located proximally of the proximal end 147 of the arm 144 when the skin sensor 131 is in its proximal position relative to the needle cover 106. One advantage of such an embodiment is that the skin sensor 131 may be able to move further in the distal direction before the needle cover 106 can disengage with the housing 101 to move back towards the extended position, as will be explained in more detail hereinafter.

As shown in FIG. 3, the skin sensor 131 may comprise a plurality of reinforcing members 164. The plurality of reinforcing members 164 may be spaced circumferentially about the body portion 141 of the skin sensor 131. The plurality of reinforcing members 164 may be spaced equidistantly about the longitudinal axis X of the medicament delivery device 100. In embodiments where two reinforcing members 164 are present, the reinforcing members 164 may be located diametrically opposite each other.

In some embodiments, the skin sensor 131 may comprise a flange 169. The flange 169 may be a part of the body portion 161 of the skin sensor 131 that extends beyond the reinforcing member 164. The flange 169 may extend radially outwardly relative to the reinforcing member 164 of the skin sensor 131. The flange 169 may be configured to abut against a distal end 108 of the needle cover 106 when the skin sensor 131 is in the proximal position relative to the needle cover 106. Therefore, once the required proximal movement of the skin sensor 131 has been achieved, any further compressive force applied by an operator of the medicament delivery device 100 may be transferred to the needle cover 106 to begin compressing the needle cover biasing member 111.

As shown in FIG. 3 and FIGS. 4A to 4E, the reinforcing member 164 of the skin sensor 131 may be located in the slot 155 in the body portion 141 of the needle cover 106. The slot 155 may be configured to allow the reinforcing member 164 to move axially therethrough. Thus, the reinforcing member 164 of the skin sensor 131 may be located radially inward of the arm 144 of the needle cover 106.

Referring briefly to FIG. 4C, the housing 101 may comprise a catch 171. The catch 171 may be configured to cooperate with the projection 148 of the needle cover 106 when the needle cover 106 is in the retracted position and the skin sensor 131 is in its proximal position. In some embodiments, the catch 171 may be formed by a recess 172 in the inner surface 173 of the housing 101. Alternatively, the catch 171 may be formed by a protrusion (not shown) extending from the inner surface 173 of the housing 101.

The catch 171 may be formed by a proximally facing surface 174 of the recess 172. The proximally facing surface 174 may extend in a plane extending transversely to the longitudinal axis X of the medicament delivery device 100. The catch 171 may be located at an axial location in the housing 101 where the projection 148 of the needle cover 106 is located when the needle cover 106 is in its retracted position. In alternative embodiments, the catch 171 may be profiled to match the surface profile of the projection 148 of the needle cover 106. That is, the geometry of the recess 172 may be profiled to match the shaped of the projection 148 of the needle cover 106.

The housing 101 may further comprise a distally located recess 175. The distally located recess 175 may comprise an inclined surface 176 forming the upper wall of the recess 175.

The retaining mechanism 135 may comprise the proximally extending arm 144 of the needle cover 106, the projection 148 located on the proximal end 147 of the arm 144, and the catch 171 located on the inner surface 173 of the housing 101. The projection 148 may be configured to engage the catch 171 when the needle cover 106 is in its retracted position, as shown in FIG. 4C.

In some embodiments, the retaining mechanism 135 may comprise the proximally extending reinforcing member 164 of the skin sensor 131. The reinforcing member 164 may be configured to prevent the projection 148 from disengaging from the catch 171 when the needle cover 106 is held in the retracted position and the skin sensor 131 is held in the proximal position.

Referring to FIG. 4A, a schematic view of the distal end of the medicament delivery device 100 is shown. In FIG. 4A, the needle cover biasing member 111 is extended such that the needle cover 106 is located in its extended position. The needle cover biasing member 111 may act on a proximal facing surface 145 of the body portion 141 of the needle cover 106 and on a structural element 181 of the housing 101. The needle cover biasing member 111 may be located radially inwardly of the arm 144 of the needle cover 106.

In FIG. 4A, the skin sensor biasing member 132 is extended such that the skin sensor 131 is in its distal position. That is, the skin sensor biasing member 132 biases the skin sensor 131 away from the needle cover 106. The skin sensor biasing member 132 may act on a proximal facing surface 165 of the skin sensor 131 and on distal facing surface 143 of the needle cover 106. The skin sensor biasing member 132 may be located radially inwardly of the reinforcing member 164 of the skin sensor 131. The reinforcing member 164 of the skin sensor 131 may extend through the slot 155 in the body portion 141 of the needle cover 106.

When the medicament delivery device 100 is in this state shown in FIG. 4A, i.e. before use, the proximal end 167 of the reinforcing member 164 of the skin sensor 131 may be located distally from the proximal end 147 of the arm 144 of the needle cover 106. In addition, the projection 148 on the arm 144 of the needle cover 106 may be located in the distally located recess 175.

In embodiments where the arm 144 is biased inwardly, the proximal end of the arm 144 may be originally inclined relative to the longitudinal axis X of the medicament delivery device 100.

Referring to FIG. 4B, upon placement of the medicament delivery device 100 against an injection site, downward pressure on the device 100 may cause the skin sensor biasing member 132 to compress. Thus, the skin sensor 131 may be moved from its distal position, as shown in FIG. 4A, to its proximal position, shown in FIG. 4B, against the biasing force of the skin sensor biasing member 132.

In some embodiments, due to the difference in the spring rates of the needle cover biasing member 111 and the skin sensor biasing member 132, the skin sensor biasing member 132 may be moved to its compressed state before any substantial compression of the needle cover biasing member 111. In some embodiments, due to the different initial compressions of the needle cover biasing member 111 and the skin sensor biasing member 132, the skin sensor biasing member may be moved to its compressed state before any further substantial compression of the needle cover biasing member 111 occurs. It will be appreciated that the compressed state of the biasing members may refer to the maximum compression achieved within the operation of the medicament delivery device 100 rather than the total overall compression achievable by the skin sensor biasing members.

Therefore, the skin sensor 131 may be moved into its proximal position relative to the needle cover 106 before the needle cover 106 is moved from its extended position. As shown in FIG. 4B, the proximal ends 147, 167 of the needle cover 106 and the skin sensor 131 may be located in the same plane extending transversely to the longitudinal axis X of the medicament delivery device 100. Additionally, the projection 148 of the needle cover 106 remains in the distally located recess 175.

In embodiments where the arm 144 is biased inwardly, movement of the skin sensor 131 into its proximal position may bias the proximal end of the arm 144 outwards such that the proximal end of the arm 144 extends parallel to the longitudinal axis X of the medicament delivery device 100.

Referring now to FIG. 4C, the needle cover 106 has been moved from its extended position to its retracted position. The skin sensor 131 may move together with the needle cover 106 such that the proximal ends 147, 167 of the needle cover 106 and the skin sensor 131 remain located in the same plane extending transversely to the longitudinal axis X of the medicament delivery device 100. In some embodiments, the proximal end 167 of the reinforcing arm 167 may be located proximally of the proximal end 147 of the arm 144 of the needle cover 106.

During movement from the state shown in FIG. 4B to the state shown in FIG. 4C, the second engaging surface 152 of the projection 148 on the needle cover 106 engages with the inclined surface 176 of the recess 175. As the needle cover 106 is moved proximally against the biasing force of the needle cover biasing member 111, the inclined surface 176 of the recess 175 may act as a ramp. The interaction between the inclined surface 176 and engaging surface 152 of the projection 148 causes the arm 144 of the needle cover 106 and the reinforcing member 164 of the skin sensor 131 to deflect inwards toward the longitudinal ais X of the medicament delivery device 100.

When the needle cover 106 is located in the retracted position, as shown in FIG. 4C, the projection 148 may be located in the recess 172. In this position, the projection 148 may be configured to engage the catch 171. That is, the first engaging surface 151 of the projection 148 may contact the proximally facing surface 174 of the recess 172. The reinforcing member 164 of the skin sensor 131 may prevent the projection 148 disengaging from the catch 171 when the needle cover 106 is held in the retracted position and the skin sensor 131 is in its proximal position relative to the needle cover 106. Thus, the biasing force of the needle cover biasing member 111 may be transferred to the housing 101 of the medicament delivery device 100. This may reduce the hold force required by the user during operation of the medicament delivery device 100.

For example, whilst the projection 148 is located in the recess 172, the needle cover biasing member 111 exerts a force on the needle cover 106 in an attempt to return the needle cover 106 to its extended position. However, the projection 148 abuts against the proximally facing surface 174 o the recess 172 such that the force of the needle cover biasing member 111 is transferred to the housing 101. Due to the inclined first engaging surface 151 of the projection 148, the distally acting force of the needle cover biasing member 111 can cause the first engaging surface 151 of the projection to slide against the catch 171, which may result in the proximal end of the arm 144 deflecting inwards. Sufficient distal movement of the needle cover 106 would result in the projection 148 disengaging with the catch 171.

However, the reinforcing member 164 of the skin sensor 131 may abut the inner surface of the arm 144. Thus, the skin sensor 131 may be configured to prevent the inward deflection of the projection 148 and proximal end of the arm 144 under the distally acting force of the needle cover biasing member 111. In some embodiments, the reinforcing member 164 of the skin sensor 131 may be stiffer than the arm 144 of the needle cover 106. Thus, as the projection 148 cannot be disengaged with the catch 171 when the needle cover 106 is in the retracted position and the skin sensor 131 is in the proximal position relative to the needle cover 106, the biasing force of the needle cover biasing member 111 may be transferred to the housing 101.

Figure 4D:
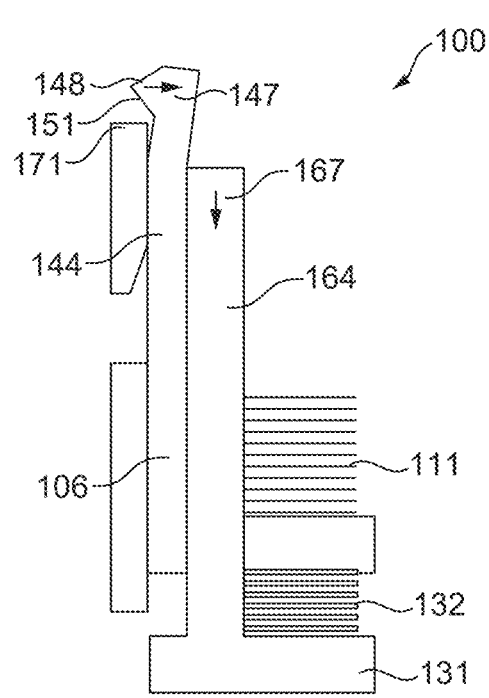

Referring now to FIG. 4D, once the medicament delivery device 100 is removed from the injection site, the compressive forces on the needle cover biasing member 111 and the skin sensor biasing member 132 are removed. Due to the reinforcing member 164 holding the projection 148 in engagement with the catch 171, the needle cover 106 cannot move distally. However, there is no longer a compressive force acting on the skin sensor 131. Therefore, the skin sensor biasing member 132 is able to extend. Thus, the skin sensor 131 may be moved into its distal position relative to the needle cover 106 under the force of the skin sensor biasing member 132.

When the skin sensor 131 is in its distal position relative to the needle cover 106, the proximal end 167 of the reinforcing member 164 of the skin sensor 131 is moved distally relative to the proximal end 147 of the arm 144 of the needle cover 106. That is, the proximal end 167 of the reinforcing member 164 of the skin sensor 131 is located distally relative to the deflectable proximal end 147 of the arm 144 of the needle cover 106. Thus, the skin sensor 131 may no longer be able to prevent the inward deflection of the projection 148 and proximal end of the arm 144 under the distally acting force of the needle cover biasing member 111. Due to the inclined first engaging surface 151 of the projection 148, the distally acting force of the needle cover biasing member 111 may cause the first engaging surface 151 of the projection to slide against the catch 171. As a result, when the needle cover 106 is in the retracted position and the skin sensor 131 is in the proximal position relative to the needle cover 106, the proximal end of the arm 144 may be deflected inwards. The needle cover biasing member 111 may then bias the needle cover 106 back towards the extended position.

Figure 4E:
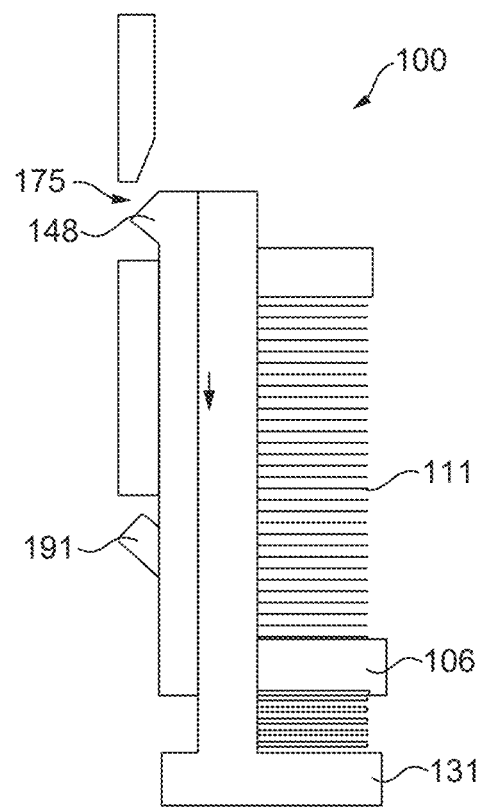

Referring briefly to FIG. 4E, the medicament delivery device 100 is shown once the needle cover biasing member 111 has returned the needle cover to the extended position and the projection 148 has re-entered the recess 175. The skin sensor 131 is in its distal position relative to the needle cover 106.

The medicament delivery device 100 may further comprise a needle cover lock 191. The needle cover lock 191 may be configured to prevent proximal movement of the needle cover 106 once the needle cover 106 is in the extended position post-use.

Although described previously in detail, a brief description of the method of preparing a medicament delivery device 100 for use will be described hereinafter. The method comprises moving a skin sensor 131 proximally from a distal position to a proximal position against the force of a skin sensor biasing member 132. The method further comprises moving the skin sensor 132 and a needle cover 106 proximally from an extended position to a retracted position within a housing 101. The method further comprises engaging a projection 148 on an arm 144 of the needle cover 106 with a catch 171 located in the housing 101 and maintaining the projection 148 in engagement with the catch 171 with a reinforcing member 164 of the skin sensor 131. Engaging the needle cover 106 with the housing 101 transfers the force of the needle cover biasing member 111 to the housing 101.

In addition, although described previously in detail, a brief description of the method of locking a medicament delivery device 100 after use will be describe hereinafter. The method comprises removing the medicament delivery device 100 from an injection site and moving the skin sensor 131 distally from a proximal position to a distal position under the force of a skin sensor biasing member 132. The method further comprises disengaging a projection 148 of a needle cover 106 from a catch 171 located in a housing 101, and moving the needle cover 106 in the distal direction from a retracted position to an extended position; under the biasing force of a needle cover biasing member 111. The method further comprises engaging a locking mechanism 181 to prevent proximal movement of the needle cover 106.

The features described and/or contemplated in relation to the medicament delivery device 200 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a caperturesterol-reducing antisense therapeutic for the treatment of familial hypercaperturesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014 (E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

| REFERENCE NUMERALS | |
|---|---|
| 10 | Drug Delivery Device |
| 11 | Housing |
| 12 | Cap Assembly |
| 13 | Needle Sleeve |
| 17 | Needle |
| 20 | Distal Region |
| 21 | Proximal Region |
| 22 | Button |
| 23 | Piston |
| 100 | Medicament Delivery Device |
| 101 | Housing |
| 102 | Proximal End |
| 103 | Distal End |
| 105 | Needle |
| 106 | Needle Cover |
| 107 | Distal End |
| 108 | Distal End |
| 111 | Needle Cover Biasing Member |
| 115 | Plunger Rod |
| 116 | Syringe |
| 117 | Piston |
| 119 | Collar |
| 122 | Screw Thread |
| 124 | Drive Member |

-continued

| REFERENCE NUMERALS | |
|---|---|
| 125 | Injection Site |
| 131 | Skin Sensor |
| 132 | Skin Sensor Biasing Member |
| 135 | Retaining Mechanism |
| 141 | Body Portion |
| 142 | Aperture |
| 143 | Distal Facing Surface |
| 144 | Arm |
| 145 | Proximally Facing Surface |
| 147 | Proximal End |
| 148 | Projection |
| 151 | First Engaging Surface |
| 152 | Second Engaging Surface |
| 155 | Slot |
| 161 | Body Portion |
| 162 | Distal Facing Surface |
| 163 | Aperture |
| 164 | Reinforcing Member |
| 165 | Proximal Facing Surace |
| 167 | Proximal End |
| 171 | Catch |
| 172 | Recess |
| 173 | Inner Surface |
| 174 | Proximally Facing Surface |
| 175 | Distally Located Recess |
| 176 | Inclined Surface |
| 181 | Structural Element |
| 191 | Locking Mechanism |

The invention claimed is:

1. A medicament delivery device comprising:
a housing comprising a proximal end and a distal end;
a needle and a needle cover,
wherein the needle cover is axially movable between an extended position, in which the needle cover extends from the distal end of the housing and covers a distal end of the needle, and a retracted position, in which the needle cover is located in a proximal position relative to the extended position such that the needle protrudes from a distal end of the needle cover;
a needle cover biasing member configured to bias the needle cover axially in a distal direction towards the extended position;
a skin sensor extending distally from the distal end of the needle cover and configured to contact an injection site;
a skin sensor biasing member acting between the needle cover and the skin sensor, the skin sensor biasing member being configured to bias the skin sensor axially in the distal direction from a proximal position to a distal position away from the needle cover; and
a retaining mechanism configured to temporarily retain the needle cover in the retracted position and temporarily transfer at least a part of a force of the needle cover biasing member to the housing such that the needle cover biasing member is prevented from moving the needle cover distally, wherein the retaining mechanism comprises a proximally extending arm of the needle cover, a catch located on an inner surface of the housing, and a proximally extending reinforcing member of the skin sensor, wherein a projection on a proximal end of the arm is configured to engage the catch when the needle cover is in the retracted position, wherein the reinforcing member is configured to prevent the projection from disengaging from the catch when the needle cover is held in the retracted position and the skin sensor is held in the proximal position, and wherein upon depression of the medicament delivery device against the injection site, the skin sensor is configured to be moved from the distal position to the proximal position before the needle cover is moved from the extended position to the retracted position.

2. The medicament delivery device according to claim 1, wherein the retaining mechanism is configured to transfer substantially the full force of the needle cover biasing member to the housing when the needle cover is in the retracted position and the skin sensor is in the proximal position.

3. The medicament delivery device according to claim 1, wherein the proximal end of the arm of the needle cover is deflectable in a radially inward direction.

4. The medicament delivery device according to claim 3, wherein the projection comprises an inclined engaging surface.

5. The medicament delivery device according to claim 3, wherein the proximal end of the arm of the needle cover is biased radially inwards.

6. The medicament delivery device according to claim 1, wherein the reinforcing member of the skin sensor is located radially inwards of the arm of the needle cover.

7. The medicament delivery device according to claim 6, wherein the needle cover comprises an annular member having a slot adjacent to the arm, wherein the reinforcing member of the skin sensor extends and is moveable axially through the slot.

8. The medicament delivery device according to claim 1, wherein the reinforcing member of the skin sensor is stiffer than the arm of the needle cover.

9. The medicament delivery device according to claim 1, wherein a spring rate of the needle cover biasing member is greater than a spring rate of the skin sensor biasing member.

10. The medicament delivery device according to claim 1, wherein a spring rate of the needle cover biasing member is the same as a spring rate of the skin sensor biasing member, and the needle cover biasing member has a greater amount of initial compression than the skin sensor biasing member when the needle cover is in the extended position and the skin sensor is in the distal position relative to the needle cover.

11. The medicament delivery device according to claim 1, wherein the needle cover biasing member and/or the skin sensor biasing member are coil springs.

12. The medicament delivery device according to claim 1, wherein the medicament delivery device is configured to inject greater than 2 ml of a medicament and/or wherein the medicament delivery device is configured to inject a medicament having a viscosity of greater than 25 cP.

13. The medicament delivery device according to claim 1, further comprising a needle cover lock configured to prevent proximal movement of the needle cover once the needle cover is in the extended position post-use.

14. The medicament delivery device according to claim 1, wherein the medicament delivery device comprises a medicament.

* * * * *